United States Patent [19]

van der Weijst et al.

[11] 4,329,514

[45] May 11, 1982

[54] METHOD FOR CONTROLLING RUNAWAY DECOMPOSITION IN THE PREPARATION OF HYDROCARBON HYDROPEROXIDES

[75] Inventors: Ludovicus B. J. O. van der Weijst, Klundert; Enno B. De Vries; Gerard J. Heiszwolf, both of Amsterdam, all of Netherlands

[73] Assignee: Shell Oil Company, Houston, Tex.

[21] Appl. No.: 225,939

[22] Filed: Jan. 19, 1981

[30] Foreign Application Priority Data

Jan. 21, 1980 [NL]  Netherlands ..................... 8000363

[51] Int. Cl.³ .............................................. C07C 179/02
[52] U.S. Cl. ..................... 568/577; 568/569; 568/565; 568/570; 568/571
[58] Field of Search ............... 568/569, 571, 572, 573, 568/574, 575, 577, 565, 570

[56] References Cited

U.S. PATENT DOCUMENTS

| | | | |
|---|---|---|---|
| 2,447,794 | 8/1948 | Brewer ................................. | 568/577 |
| 2,632,772 | 3/1953 | Armstrong et al. ................ | 568/573 |
| 3,160,668 | 12/1964 | Davue .................................. | 568/573 |
| 4,028,423 | 6/1977 | Brownstein ......................... | 568/571 |
| 4,071,561 | 1/1978 | Ciborowski et al. ............... | 568/573 |

FOREIGN PATENT DOCUMENTS

| | | | |
|---|---|---|---|
| 558506 | 6/1958 | Canada ................................ | 568/573 |
| 6810123 | 3/1969 | Netherlands ........................ | 568/571 |
| 7511955 | 10/1976 | Netherlands ........................ | 568/573 |
| 713138 | 8/1954 | United Kingdom ................ | 568/573 |

*Primary Examiner*—Werren B. Lone

[57] ABSTRACT

Episodes of accelerated decomposition, or runaway, during the preparation of hydrocarbon hydroperoxides by reaction of hydrocarbons with molecular oxygen at elevated temperature, are brought under control through the addition to the oxidation reaction mixture of a small quantity of base in a substantially instantaneous manner at the onset of the runaway.

7 Claims, No Drawings

METHOD FOR CONTROLLING RUNAWAY DECOMPOSITION IN THE PREPARATION OF HYDROCARBON HYDROPEROXIDES

BACKGROUND OF THE INVENTION

The invention relates to a method for the control of disturbances in the preparation of hydrocarbon hydroperoxides by oxidation of hydrocarbons with molecular oxygen. More particularly, the present invention relates to control of runaway decomposition of hydroperoxides in such preparations by a process which comprises steps for sensing the onset of runaway and, in response thereto, adding to the oxidation reaction mixture in a substantially instantaneous manner of small quantity of a base.

It is well known in the chemical arts that hydroperoxides of hydrocarbons, for example, isobutane, cyclohexane, cumene, and ethylbenzene, can be prepared by contacting the hydrocarbon with molecular oxygen at an elevated temperature. The resulting hydroperoxides have recognized value, for instance, as catalysts, as initiators for free radical-type reactions, and as starting materials or intermediates in the production of chemicals such as oxirane compounds and other hydroperoxides.

A feature of hydrocarbon hydroperoxide manufacture that is the subject of substantial concern to the art is decomposition of the hydroperoxide in the oxidation reaction mixture, which is known to occur in response to any one or more of a great number of stimuli. Under normal operation, hydrocarbon hydroperoxide preparation is accomplished in such a manner that the decomposition of the product hydroperoxide which occurs is limited to an acceptably low level. For this purpose, precautions are typically taken to insure, for instance, that reaction mixture temperature is maintained within a specified range and that hydrocarbon and oxygen reactants are essentially free of impurities known to cause the decomposition. It is also common practice to minimize this low-level decomposition by limiting residence time of the reaction, e.g., through the addition of reaction promoters which decrease the reaction's induction period and increase its rate or through a termination of the reaction at a relatively low conversion of the hydrocarbon to hydroperoxide. Nevertheless, because of misoperation, equipment failure, or the like, there occur instances of abnormal, accelerated decomposition in the reaction mixture which cannot readily be managed. This decomposition is accompanied by the formation of decomposition by-products, e.g., alcohols, organic acids, aldehydes, and ketones, and by the release of heat and a consequential increase in temperature in the reaction mixture. In such circumstances the hydroperoxide decomposition is said to be autocatalytic, since the by-product chemicals and increased temperature both promote further accelerated decomposition.

Instances of uncontrolled, accelerated decomposition of the hydroperoxidation reaction mixture are herein termed "runaway". If allowed to proceed unchecked, runaway will, of course, result in the loss of valuable hydroperoxide product. Of substantially greater concern, however, is the danger that the runaway will accelerate to explosion of the hydrocarbon hydroperoxide/oxygen/hydrocarbon mixture. In some cases, potentially explosive conditions are encountered with only moderate increases in temperature, e.g., 10° to 20° C., above that of normal operation.

There are available in the art a number of teachings directed to the management of runaway reactions in hydrocarbon hydroperoxide preparation. According to one approach to the problem, there is provided in the oxidation reactor excess heat exchange capacity which can be put into use to compensate for the heat release associated with accelerated decomposition of the hydroperoxide product. However, the effectiveness of this approach is limited, and the expense involved restricts its practical application. Another alternative for management of runaway, disclosed in Netherlands patent specification No. 7511955, relates to the introduction of substantial quantities of water into the oxidation reactor whenever runaway is encountered to dilute and cool the reaction mixture.

With respect to aspects of the present invention which relate to the addition of a base to a runaway hydroperoxide reaction mixture, it is to be noted that bases have conventionally been utilized for a variety of purposes in hydrocarbon oxidation. For instance, U.S. Pat. No. 2,632,772 teaches addition of an alkali to the reaction mixture. It is said that apart from preventing the corrosion of iron reaction vessels, the effect of this alkali addition is that the maximum rate of oxidation is higher and is obtained with a shorter induction period, and that the peroxide concentration in the reaction mixture may be greater than in the absence of alkali. On the subject of the management of runaway in the reaction, the patent teaches only that temperature should be reduced as the reaction proceeds, and that residence time of the mixture in the oxidation reactor should be limited to avoid accelerated hydroperoxide decomposition. Such measures may be undesirable, however, because of adverse influence on oxidation reaction conversion, selectivity, and rate. Great Britain Pat. No. 713,138 teaches a process for the oxidation of cumene in the presence of secondary or tertiary amine reaction promoters. The amine is added to the reaction mixture in a quantity based upon the concentration in the hydrocarbon feed of certain impurities which bind free radicals, interrupting the chain reaction mechanism by which the oxidation reaction proceeds. The patent teaches that the presence of the amines counteracts the effect of the impurities and results in a shorter reaction induction period. It is also suggested that the presence of the amines during the oxidation reaction decreases the production of color-forming reaction by-products as the result of the low-level hydroperoxide decomposition normally observed in such oxidation reactions. There is no mention in this patent of methods for bringing runaway decomposition under control.

SUMMARY OF THE INVENTION

It has now been found that instances of runaway decomposition in the preparation of hydrocarbon hydroperoxides, by oxidation of hydrocarbons at elevated temperatures, can be very effectively brought under control by the addition to the oxidation reaction mixture in a substantially instantaneous manner of a small quantity of a base. The addition of the base is made in response to changes in oxidation reaction conditions indicating the onset of runaway decomposition, for example, an uncontrolled increase in reaction mixture temperature.

DESCRIPTION OF THE PREFERRED EMBODIMENTS

The process of the invention is generally suitable for application to any of the conventional reactions for conversion of hydrocarbons to hydrocarbon hydroperoxides by reaction with molecular oxygen. Most commonly, oxidation reactions of this sort are utilized for the preparation of hydroperoxides of tertiary alkanes, cycloalkanes and aralkanes, preferably those having 4 to 20 carbon atoms. The aralkanes may contain one or more aromatic rings and may be substituted with one or more alkyl groups. Specific examples of a particularly preferred class of hydrocarbons include isobutane, isopentane, isohexane, 2,3-dimethylbutane, cumene, ethylbenzene, ethyltoluene, ethylnaphthalene, cyclopentane, methylcyclohexane, and cyclododecane. A most preferred class of hydrocarbon reactants consists of isobutane, cyclohexane, and ethylbenzene. Hydroperoxide preparation is accomplished by contact of the hydrocarbon with molecular oxygen, either substantially pure or in admixture with inert substances such as nitrogen, at elevated temperature. Often, it is the case that the oxidation is conducted in a reactor containing multiple, i.e., gas and liquid, phases. The oxidation reaction mixture, as the terminology is utilized in description of the invention, is intended to include all phases in the reactor. Hydrocarbon oxidation reactions are typically carried out at a temperature in the range of about 80° to 140° C., and at a pressure between about one and seventy bar, absolute. However, as is understood in the art, conditions for the oxidation reactions here of interest vary according to the hydrocarbon hydroperoxide that is being prepared and according to the emphasis that is placed upon particular aspects of reaction results.

The base which is added to the runaway hydrocarbon oxidation reaction mixture during practice of the invention is suitably either an inorganic or an organic base. Examples of suitable basic substances are the hydroxides, carbonates, bicarbonates, phosphates, or pyrophosphates of the alkali metals or alkaline earth metals and the alkali metal salts of organic carboxylic acids. Also suitable are the amines such as, for instance, dimethylamine, trimethylamine, triethylamine, dibutylamine, triethanolamine, piperidine, pyridine, and tetraethylenepentamine. Ammonia is a base particularly preferred for use in the invention.

For purposes of the invention, the base, suitably in the form of a gas, a liquid, a finely divided solid, or a solution, may be added directly to the reaction mixture or may be introduced into the hydrocarbon or oxygen feed stream which is in turn added to the reaction mixture. It is most desirable that the manner of addition be such that the base may be rapidly mixed into the mixture, aided, for instance, by vigorous agitation. For this reason, it is preferred that the base be added to the oxygen feed stream and further that the base be a vapor at the temperature of the oxygen stream and also at the temperature of the reaction mixture. Examples of bases which are gaseous at the relevant temperatures in most hydrocarbon oxidation reactions include dimethylamine, trimethylamine, and ammonia.

It is a critical feature of the invention that the base is added to the reaction mixture at the onset of a runaway. Determination is suitably made of the onset of runaway by means of monitoring any one or more of several reaction parameters. An important parameter in this regard is reaction mixture temperature; an uncontrolled increase in temperature of the reaction mixture, to a level significantly greater than that theretofore maintained for normal operation of the hydrocarbon hydroperoxide preparation process, is a reliable indication of accelerated decomposition of the hydroperoxide of runaway proportions. The onset of runaway can, however, also be determined by monitoring other parameters such as, for instance, composition of the reaction mixture with respect to hydroperoxide or its decomposition products.

The essentially instantaneous nature of the addition of the base is both a necessary characteristic of the process of the invention and one which provides distinction with respect to the utilization of bases in prior art processes for hydrocarbon hydroperoxide preparation. As has been heretofore noted, it is recognized in the art that various bases serve as reaction promoters for hydrocarbon oxidation. In these services, the base is added to an oxidation reaction mixture either at the beginning of the reaction or continuously or semi-continuously throughout the period of the reaction. It is found that the function of the addition of base in such a manner is in practical effect different from the function of the invention with respect to management of runaway hydroperoxide decomposition. In illustration of this difference, it is observed that, while in a given reaction mixture a specified quantity of base can be added at the onset of a runaway to bring it under control, this same quantity of base if added to the mixture either at the beginning of the oxidation or continuously throughout the reaction does not prevent a runaway from occurring. Preferably, the essentially instantaneous addition of base for purposes of the invention is made so that a quantity of base sufficient to bring a runaway under control is dispersed throughout the reaction mixture within about five minutes or less after the onset of the runaway.

The quantity of added base which is effective to bring the runaway under control, that is, to stop the uncontrolled increase of reaction mixture temperature, for purposes of the practice of the invention is generally small, e.g., between 0.5 and 20 gram-equivalents (most preferably between about 0.1 and 5 gram-equivalents) of the base per 1000 kilograms of the reaction mixture. As an example, for the use of ammonia as the base, an addition of between about one and 300 parts per million by weight (ppmw) of the reaction mixture, preferably between about 2 and 80 ppmw, via introduction into the oxygen feed stream to the reaction mixture, is generally responsible for very good results. The optimum quantity of base for a given situation will vary according to the character of the runaway encountered, for instance, according to the rate and magnitude of the temperature increase in the reaction mixture. As a rule, the quantity of base should be sufficient to stop the increase in reaction mixture temperature. If a first addition of base is not effective for this purpose, one or more further additions can be made to the reaction mixture until the runaway is brought under full control.

Following an application of the process of the invention, the oxidation reaction mixture is preferably returned to normal operating temperature. If the cause of the runaway can be identified and removed, e.g., by switching from a contaminated to an uncontaminated feed, the oxidation of the reaction mixture can, in principle, be continued. However, because of the contamination of the reaction mixture in such a case, it is to be expected that runaway conditions will reoccur. Consequently, it is generally preferred that, after the addition of the base, the introduction of oxygen reactant be reduced or discontinued and the mixture cooled to a temperature at which essentially no further reaction occurs.

The following examples are provided to illustrate certain aspects of the process of the invention.

EXAMPLE I

A reactor in which a distributor for the introduction of a gas and a stirrer had been installed, was charged with 1 liter of ethylbenzene to which 1.5 ppm of sulfur in the form of 2,5-dimethylthiophene had been added. Under the conditions at which ethylbenzene oxidation is carried out, this sulfur compound promotes the decomposition of the ethylbenzene hydroperoxide formed. At a constant temperature of 150° C. and at a pressure of 3 bar abs., 80 liters per hour of a mixture consisting of air and nitrogen was passed through the ethylbenzene. The ratio between the quantities of air and nitrogen was adjusted in such a way that the oxygen concentration in the off-gas from the reactor was 4 percent by volume. After 90 minutes, there occured in the reaction mixture a relatively sudden, uncontrolled departure from constant temperature operation. After another 15 minutes, i.e., at a total reaction time of 105 minutes, temperature had risen to 152° C. The onset of runaway was indicated by this uncontrolled increase in reaction mixture temperature and/or by a substantial rapid increase in the composition of the mixture with respect to ethylbenzene hydroperoxide decomposition products, e.g., phenol. Therefore, at this time, 10 ppm NH₃ (based on the weight of the reaction mixture) were added to the mixture via the air and nitrogen feed stream. While no other measures were taken to reduce the temperature of the mixture and the flow of oxygen reactant was not discontinued, the temperature started to fall and had returned to the desired 150° C. after another ten minutes. Control over the accelerated decomposition in the reaction mixture was thus effective.

The oxidation reaction was continued at 150° C. Since the 2,5-dimentylthiopene remained in the reaction mixture, onset of runaway was again observed at 125 and 150 minutes. In each instance, a further addition of 10 ppm NH₃ was made to bring the runaway decomposition under control.

The results of Example I are summarized in Table A, which also illustrates phenol content of the reaction mixture, a measure of the decomposition of the hydroperoxide.

TABLE A

| Reaction time in min. | Temperature, °C. | Phenol content, % by wt | Ethylbenzene hydroperoxide % by wt |
|---|---|---|---|
| 90 | 150 | 0.06 | 7.3 |
| 105 | 152* | 0.22 | 8.3 |
| 115 | 150 | 0.32 | 9.0 |
| 125 | 152* | 0.72 | 8.9 |
| 135 | 151 | — | — |
| 150 | 153* | 1.6 | 8.3 |
| 180 | 152 | 2.1 | 7.5 |

(a) Uncontrolled temperature increases indicating the onset of runaway.

Example I shows that the instantaneous addition of a very small quantity of base is effective to limit the decomposition of the hydrocarbon hydroperoxide and to check the uncontrolled rise in temperature in the reaction mixture.

For purposes of comparison, an experiment was conducted in which the oxidation of ethylbenzene was repeated according to the general procedures of Example I. However, in this case, no base was added to the reaction mixture at the onset of runaway decomposition. As indicated in Table B, the decomposition of ethylbenzene hydroperoxide and the temperature increase in the reaction mixture were both substantially greater than in Example I.

TABLE B

| Reaction time in min. | Temperature °C. | Phenol content, % by wt. | Ethylbenzene hydroperoxide content % by wt. |
|---|---|---|---|
| 60 | 150 | ≦0.05 | 5.3 |
| 90 | 150 | ≦0.05 | 8.7 |
| 105 | 151 | 0.22 | 10.0 |
| 115 | 153 | 0.85 | 9.4 |
| 125 | 155 | 1.8 | 7.3 |
| 135 | 153 | 2.7 | 5.5 |
| 150 | 150 | 3.4 | 3.8 |
| 180 | 149 | 4.1 | 1.6 |

EXAMPLE II

In the manner described in Example I, ethylbenzene, to which 1.5 ppm of sulphur had been added as 2,5-dimethylthiophene, was oxidized at a temperature of 150° C. and a pressure of 3 bar abs. After a reaction time of 90 minutes the temperature started to rise and reached 152° C. after a reaction time of 106 minutes. At this moment 10 ppm of NH₃ (based on the weight of the reaction mixture) were added to the mixture via the stream of air and nitrogen. The mixture was cooled. The results are summarized in Table C.

TABLE C

| Reaction time in min. | Temperature, °C. | Phenol content, % by wt. | Ethylbenzene hydroperoxide content, % by wt. |
|---|---|---|---|
| 90 | 150 | 0.06 | 7.6 |
| 106 | 152* | 0.39 | 8.6 |
| 121 | 141 | 0.67 | 9.0 |
| 151 | 142 | 1.2 | 8.7 |
| 181 | 138 | 1.9 | 7.8 |

*Uncontrolled temperature increase indicating the onset of runaway.

EXAMPLE III

In the manner described in Example I, ethylbenzene, to which 1.5 ppm of sulphur had been added as 2,5-dimethylthiophene, was oxidized at a temperature of 150° C. and a pressure of 3 bar abs. After a reaction time of 84 minutes the temperature began to rise and reached 152° C. after 95 minutes. At this moment 20 ppm of NH₃ were added to the gas stream and the reactor was cooled. Three minutes after the NH₃ injection, the flow of the air to the reactor was discontinued and only nitrogen was passed through the reactor. The results are summarized in Table D.

TABLE D

| Reaction time in min. | Temperature, °C. | Phenol content, % by wt | Ethylbenzene hydroperoxide content, % by wt |
|---|---|---|---|
| 90 | 151 | 0.34 | 5.9 |
| 95* | 152 | 0.54 | 6.1 |
| 98 | 150 | — | — |
| 110 | 140 | 0.52 | 6.0 |
| 140 | 140 | 0.54 | 5.7 |
| 170 | 140 | 0.55 | 5.4 |

*Uncontrolled temperature increase indicating the onset of runaway.

Table D illustrates not only that the runaway decomposition of the reaction mixture is effectively brought under control but also that essentially all decomposition in the mixture is stopped by practice of the base addition in accordance with the invention together with a cooling of the reaction mixture and a discontinuation of the flow of molecular oxygen-containing gas. The three steps in combination, i.e., base addition, cooling, and discontinuation of oxygen flow, are responsible for a very beneficial effect in this regard—an effect which cannot be achieved by the practice of any single step or combination of two of these steps.

Repetition of Example III with a base addition of 10 ppmw of ammonia yielded essentially the same results.

For purposes of comparison, an experiment was carried out in the manner of Example III, but without addition of base to the reaction mixture. After a reaction time of 95 minutes, the reaction mixture was cooled; after 97 minutes the flow of air to the reaction mixture was discontinued. Table E summarizes the results of this comparative experiment.

TABLE E

| Reaction time in min. | Temperature, °C. | Phenol content, % by wt | Ethylbenzene hydroperoxide content, % by wt |
|---|---|---|---|
| 60 | 150 | 0.05 | 4.6 |
| 90 | 151 | 0.42 | 6.1 |
| 95 | 152 | 0.72 | 6.0 |
| (cooling) | | | |
| 97 | | — | — |
| (no air) | | | |
| 100 | 154 | — | — |
| 106 | 153 | — | — |
| 115 | 145 | — | — |
| 120 | 140 | 1.8 | 2.5 |
| 180 | 140 | 2.0 | 1.3 |
| 240 | 140 | 2.1 | 0.9 |

An experiment was conducted according to the general procedures of Example III, but without addition of base and without application of heat exchange in attempt to stop the accelerated hydroperoxide decomposition. The flow of air to the mixture was discontinued after 110 minutes. Results are summarized in Table F.

TABLE F

| Reaction time in min. | Temperature, °C. | Phenol content, % by wt | Ethylbenzene hydroperoxide content, % by wt |
|---|---|---|---|
| 90 | 150 | 0.05 | 8.3 |
| 110 | 152 | 0.41 | 9.4 |
| (no air) | | | |
| 120 | 157 | 1.4 | 5.8 |
| 135 | 151 | 1.9 | 3.4 |
| 150 | 149 | 2.2 | 2.5 |
| 180 | 150 | 2.3 | 1.6 |

EXAMPLE IV

According to the general procedures of Example I, ethylbenzene, to which 1.5 ppm of sulphur had been added as 2,5-dimethylthiophene, was oxidized at a temperature of 150° C. After a reaction time of 80 minutes the temperature started to rise. The increase in temperature was aided by a slight external heating of the mixture, so that the temperature reached a value of 162° C. at 120 minutes. At this time, 10 ppm of ammonia were added to the reaction mixture via the air/nitrogen stream. The temperature immediately started to fall. With cooling, the reaction mixture temperature reached 140° C. in 20 minutes and was then maintained at 140° C. for an additional hour. During the cooling and the subsequent hour, the flow of air and nitrogen to the reaction mixture was continued so that the oxygen concentration in the off-gas was 4 percent by volume.

The results of Example IV, showing that it is possible to regain control of a runaway at relatively high temperature by practice of the invention, are presented in Table G.

TABLE G

| Reaction time in min. | Temperature, °C. | Phenol content, % by wt | Ethylbenzene hydroperoxide content, % by wt |
|---|---|---|---|
| 60 | 150 | ≦0.05 | 4.7 |
| 80 | 151 | — | — |
| 90 | 152 | 0.14 | 7.5 |
| 100 | 157 | 0.40 | 7.8 |
| 110 | 161 | 1.2 | 6.8 |
| 120 | 162 | 2.3 | 4.3 |
| 140 | 139 | 2.5 | 4.2 |
| 170 | 140 | 2.5 | 4.2 |
| 200 | 140 | 2.7 | 4.2 |

EXAMPLE V

In the general manner described for Example I, ethylbenzene, to which 1.5 ppm of sulphur had been added as 2,5-dimethylthiophene, was oxidized at a temperature of 150° C. To the mixture of air and nitrogen 0.25 nml of gaseous $NH_3$ was added every 2.5 minutes, so that after 2 hours 10 ppm, based on the ethylbenzene, had been added. Table H shows that a runaway cannot be prevented by this semi-continuous addition of $NH_3$.

TABLE H

| Reaction time in min. | Temperature, °C. | Phenol content, % by wt | Ethylbenzene hydroperoxide content, % by wt |
|---|---|---|---|
| 60 | 150 | ≦0.05 | 4.3 |
| 90 | 150 | ≦0.05 | 7.0 |
| 120 | 154 | 0.44 | 7.6 |
| 150 | 152 | 2.6 | 2.1 |

We claim as our invention:

1. In the preparation of a hydrocarbon hydroperoxide by reacting in an oxidation reaction mixture a hydrocarbon with molecular oxygen at an elevated temperature, the process for management of runaway decomposition in the reaction mixture which comprises the steps of sensing the onset of runaway decomposition and in response thereto adding to the reaction mixture in a substantially instantaneous manner a quantity of base effective to bring the runaway under control, said quantity of base being between about 0.05 and 20 gram-equivalents per 1000 kilograms of the reaction mixture.

2. The process of claim 1, wherein the onset of runaway is sensed by monitoring the reaction mixture temperature for an uncontrolled increase.

3. The process of claim 2, wherein the substantially instantaneous addition of base to the reaction mixture is essentially completed within a period of five minutes.

4. The process of claim 3, wherein the quantity of added base is between about 0.1 and 5 gram equivalents per 1000 kilograms of the reaction mixture.

5. The process of claim 2, wherein the base is ammonia, added to the reaction mixture in a quantity between 1 and 300 parts per million by weight, based on the total reaction mixture.

6. The process of claim 5, wherein the quantity of ammonia is between about 2 and 80 parts per million by weight, based on the total reaction mixture.

7. In the preparation of a hydrocarbon hydroperoxide by reacting in an oxidation reaction mixture a hydrocarbon with molecular oxygen at an elevated temperature by continually passing a flow of molecular oxygen to the mixture, the process for management of runaway decomposition in the reaction mixture which comprises the steps of (1) sensing the onset of runaway decomposition, and in response thereto (2) adding to the reaction mixture in a substantially instantaneous manner a quantity of base effective to bring the runaway decomposition under control, said quantity of base being between about 0.5 and 20 gram-equivalents per 1000 kilograms of the reaction mixture, (3) discontinuing the flow of molecular oxygen to the reaction mixture, and (4) cooling the reaction mixture.

\* \* \* \* \*